(12) United States Patent
Hipskind et al.

(10) Patent No.: US 7,981,892 B2
(45) Date of Patent: Jul. 19, 2011

(54) DISUBSTITUTED PHTHALAZINE HEDGEHOG PATHWAY ANTAGONISTS

(75) Inventors: Philip Arthur Hipskind, New Palestine, IN (US); Takako Wilson (nee Takakuwa), Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/935,655

(22) PCT Filed: Apr. 1, 2009

(86) PCT No.: PCT/US2009/039065
§ 371 (c)(1),
(2), (4) Date: Sep. 30, 2010

(87) PCT Pub. No.: WO2009/134574
PCT Pub. Date: Nov. 5, 2009

(65) Prior Publication Data
US 2011/0046143 A1      Feb. 24, 2011

Related U.S. Application Data

(60) Provisional application No. 61/048,729, filed on Apr. 29, 2008.

(51) Int. Cl.
*A01N 43/58* (2006.01)
*A61K 31/50* (2006.01)
*C07D 237/30* (2006.01)

(52) U.S. Cl. ........................ 514/248; 544/237

(58) Field of Classification Search .................. 544/237; 514/248
See application file for complete search history.

(56) References Cited

U.S. PATENT DOCUMENTS

| 3,753,988 A | 8/1973 | Rodway et al. |
| 5,985,878 A | 11/1999 | Stokbroekx et al. |
| 6,432,970 B2 | 8/2002 | Beachy et al. |
| 2009/0048259 A1 | 2/2009 | Austin et al. |
| 2010/0324048 A1 | 12/2010 | Hipskind et al. |

FOREIGN PATENT DOCUMENTS

| WO | WO 97/26258 A1 | 7/1997 |
| WO | WO 99/52534 A1 | 10/1999 |
| WO | WO 00/74706 A1 | 12/2000 |
| WO | WO 03/088970 A2 | 10/2003 |
| WO | WO 2004/020599 A2 | 3/2004 |
| WO | 2005/033288 | 4/2005 |
| WO | WO 2005/080378 A1 | 9/2005 |
| WO | WO 2006/004589 A2 | 1/2006 |
| WO | 2006/028958 | 3/2006 |
| WO | WO 2008/028689 A1 | 3/2008 |
| WO | 2008/110611 | 9/2008 |
| WO | 2009/002469 | 12/2008 |
| WO | WO 2009/035568 A1 | 3/2009 |
| WO | WO 2009/134574 A2 | 11/2009 |
| WO | WO 2010/007120 A1 | 1/2010 |
| WO | WO 2010/056588 A1 | 5/2010 |
| WO | WO 2010/056620 A1 | 5/2010 |
| WO | WO 2010/062507 A1 | 6/2010 |

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.TheOncologist.com].*
Frank-Kamenetsky, M., et al., "Small-molecular modulators of Hedgehog signaling: identification and characterization of Smoothened agonists and antagonists," Journal of Biolology vol. 1, Issue 2, Article 10, pp. 10.1-10.19 (2002).
Lee, J., et al., "A small-muleclar antagonist of the Hedgehog signaling pathway," ChemBioChem, vol. 8, pp. 1916-1919 (2007).
Tremblay, M., et al., "Semisynthetic cyclopamine analogues as potent and orally bioavailable Hedgehog pathway antagonists," J. Med. Chem., vol. 51, pp. 6646-6649 (2008).
Tremblay, M., et al., "Recent patents for Hedgehog pathway inhibitors for the treatment of malignancy," Expert Opin. Ther. Patents 19(8):1039-1056 (2009).

* cited by examiner

*Primary Examiner* — Paul V. Ward
(74) *Attorney, Agent, or Firm* — Danica Hostettler; John C. Demeter

(57) ABSTRACT

The present invention provides novel 1,4-disubstituted phthalazine hedgehog pathway antagonists useful in the treatment of cancer.

19 Claims, No Drawings

DISUBSTITUTED PHTHALAZINE HEDGEHOG PATHWAY ANTAGONISTS

This application is a 35 U.S.C. 371 National Stage Filing of PCT/US2009/039065 filed Apr. 1, 2009, which claims priority to U.S. Provisional Application No. 61/048,729, filed Apr. 29, 2008.

The present invention relates to Hedgehog pathway antagonists and, more specifically, to novel disubstituted phthalazines and therapeutic use thereof The Hedgehog (Hh) signaling pathway plays an important role in embryonic pattern formation and adult tissue maintenance by directing. cell. differentiation and proliferation. The Hedgehog (Hh) protein family, which includes Sonic Hedgehog (Shh), Indian Hedgehog (Ihh), and Desert Hedgehog (Dhh) are secreted glycoproteins that undergo post-translational modifications, including autocatalytic cleavage and coupling of cholesterol to the amino-terminal peptide to form the fragment that possesses signaling activity. Hh binds to the twelve-pass transmembrane protein Ptch (Ptch1 and Ptch2), thereby alleviating, Ptch-mediated suppression of Smoothened (Smo), Smo activation triggers a series of intracellular events culminating in the stabilization of the Gli transcription factors (Gli1, Gli2 and Gli3) and the expression of Gli-dependent genes that are responsible for cell proliferation, cell survival, angiogenesis and invasion.

Hh signaling has recently attracted considerable interest based on the discovery that aberrant activation of Shh signaling leads to the formation of various tumors, e.g., pancreatic cancer, medulloblastoma, basal cell carcinoma, small cell lung cancer, and prostate cancer. Several Hh antagonists have been reported in the art, such as the steroidal alkaloid compound IP-609, the aminoproline compound CUR61414; and the 2,4-disubstituted thiazole compound JK18. WO2005033288 discloses certain 1,4-disubstituted phthalazine compounds asserted to be hedgehog antagonists.

There still exists a need for potent hedgehog pathway inhibitors, particularly those having desirable pharmacodynamic, pharmacokinetic and toxicology profiles. The present invention provides novel 1,4-disubstituted phthalazines that are potent antagonists of this pathway.

The present invention provides a compound of Formula I:

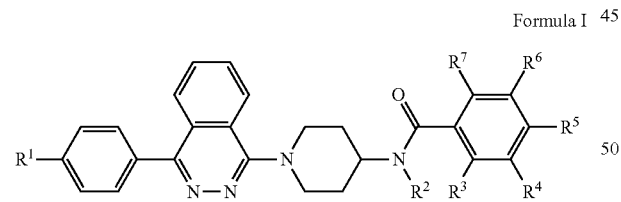

Formula I wherein:
$R^1$ is hydrogen, fluoro, cyano, trifluoromethyl, methox), or trifluoromethoxy;
$R^2$ is hydrogen or methyl; and
$R^3$, $R^4$, $R^5$, $R^6$ and $R^7$ are independently hydrogen, chloro, fluoro, cyano, trifluoromethyl or trifluoromethoxy, provided that at least two of $R^3$, $R^4$, $R^5$, $R^6$ and $R^7$ are hydrogen;
or a pharmaceutically acceptable salt thereof.

It will be understood by the skilled artisan that the compounds of the present invention comprise a tertiary amine moiety and are capable of reaction with a number of inorganic and organic acids to form pharmaceutically acceptable acid addition salts. Such pharmaceutically acceptable acid addition salts and common methodology for preparing them are well known in the art. See, e.g., P. Stahl, et at., HANDBOOK OF PHARMACEUTICAL SALTS: PROPERTIES, SELECTION AND USE, (VCHA/Wiley-VCH 2002); S. M. Berge, et al., "Pharmaceutical Salts," *Journal of Pharmaceutical Sciences*, Vol 66, No. 1, January 1977.

Specific embodiments of the invention include a compound of Formula I, or a pharmaceutically acceptable salt thereof, wherein:
(a) $R^1$ is hydrogen;
(b) $R^1$ is fluoro;
(c) $R^2$ is hydrogen;
(d) $R^2$ is methyl;
(e) $R^3$ is chloro, fluoro, trifluoromethyl, or trifluoromethox);
(f) $R^5$ is fluoro, trifluoromethoxy, or trifluoromethyl;
(g) $R^1$ is hydrogen, and $R^2$ is hydrogen;
(h) $R^1$ is fluoro, and $R^2$ is hydrogen;
(i) $R^1$ is hydrogen, and $R^2$ is methyl;
(j) $R^1$ is fluoro and $R^2$ is methyl;
(k) $R^1$ is hydrogen and $R^3$ is chloro, fluoro, trifluoromethyl, or trifluoromethoxy; (p1 (l) $R^1$ is fluoro and $R^3$ is chloro, fluoro, trifluoromethyl, or trifluoromethoxy;
(m) $R^2$ is hydrogen and $R^3$ is chloro, fluoro, trifluoromethyl, or trifluoromethoxy;
(n) $R^2$ is methyl and $R^3$ is chloro, fluoro, trifluoromethyl or trifluoromethoxy;
(o) $R^1$ is hydrogen and $R^5$ is fluoro, trifluoromethoxy, or trifluoromethyl;
(p) $R^1$ is fluoro and $R^5$ is fluoro, trifluoromethoxy, or trifluoromethyl;
(q) $R^2$ is hydrogen and $R^5$ is fluoro, trifluoromethoxy, or trifluoromethyl;
(r) $R^2$ is methyl and $R^5$ is fluoro, trifluoromethoxy, or trifluoromethyl;
(s) $R^3$ is chloro, fluoro, trifluoromethyl or trifluoromethoxy and $R^5$ is fluoro, trifluoromethoxy, or trifluoromethyl;
(t) $R^1$ is hydrogen, $R^2$ is hydrogen, and $R^3$ is chloro, fluoro, trifluoromethyl, or trifluoromethoxy;
(u) $R^1$ is hydrogen, $R^2$ is methyl, and $R^3$ is chloro, fluoro, trifluoromethyl, or trifluoromethoxy;
(v) $R^1$ is fluoro, $R^2$ is hydrogen, and $R^3$ is chloro, fluoro, trifluoromethyl, or trifluoromethoxy;
(w) $R^1$ is fluoro, $R^2$ is methyl, and $R^3$ is chloro, fluoro, trifluoromethyl, or trifluoromethoxy;
(x) $R^1$ is hydrogen, $R^2$ is hydrogen, and $R^5$ is fluoro, trifluoromethyl, or trifluoromethoxy;
(y) $R^1$ is hydrogen, $R^2$ is methyl, and $R^5$ is fluoro, trifluoromethyl, or trifluoromethoxy;
(z) $R^1$ is fluoro, $R^2$ is hydrogen, and $R^5$ is fluoro, trifluoromethyl, or trifluoromethoxy;
(aa) $R^1$ is fluoro, $R^2$ is methyl, and $R^5$ is fluoro, trifluoromethyl, or trifluoromethoxy;
(bb) $R^1$ is hydrogen, $R^2$ is hydrogen, $R^3$ is chloro, fluoro, trifluoromethyl, or trifluoromethoxy and $R^5$ is fluoro, trifluoromethyl, or trifluoromethoxy;
(cc) $R^1$ is hydrogen, $R^2$ is methyl, $R^3$ is chloro, fluoro, trifluoromethyl, or trifluoromethoxy, and $R^5$ is fluoro, trifluoromethyl, or trifluoromethoxy;
(dd) $R^1$ is fluoro, $R^2$ is hydrogen, $R^3$ is chloro, fluoro, trifluoromethyl, or trifluoromethoxy, and $R^5$ is fluoro, trifluoromethyl, or trifluoromethoxy;
(ee) $R^1$ is fluoro, $R^2$ is methyl, $R^3$ is chloro, fluoro, trifluoromethyl, or trifluorametrhoxy, and $R^5$ is fluoro, trifluoromethyl, or trifluoromethoxy;
(ff) $R^1$ is hydrogen, $R^2$ is hydrogen, $R^3$ is trifluoromethyl, and $R^5$ is fluoro;

(gg) $R^1$ is fluoro, $R^2$ is hydrogen, $R^3$ is trifluoromethyl, and $R^5$ is fluoro;
(hh) $R^1$ is hydrogen, $R^2$ is methyl, $R^3$ is trifluoromethyl, and $R^5$ is fluoro;
(ii) $R^1$ is fluoro, $R^2$ is methyl, $R^3$ trifluoromethyl, and $R^5$ is fluoro;
(jj) three of $R^3$, $R^4$, $R^5$, $R^6$ and $R^7$ are hydrogen; and
(kk) four of $R^3$, $R^4$, $R^5$, $R^6$ and $R^7$ are hydrogen.

The present invention also provides a pharmaceutical composition comprising a compound of Formula I, or a pharmaceutically acceptable salt thereof, in combination with a pharmaceutically acceptable excipient, carrier or diluent.

The compounds of the present invention are preferably formulated as pharmaceutical compositions administered by a variety of routes. Preferably, such compositions are for oral or intravenous administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995).

The present invention also provides a method of treating medulloblastoma, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer or melanoma in a mammal comprising administering to a mammal in need of such treatment an effective amount of a compound of Formula I, or a pharmaceutically acceptable salt thereof.

It will be understood that the amount of the compound actually administered will be determined by a physician under the relevant circumstances, including the condition to be treated, the chosen route of administration, the actual compound or compounds administered, the age, weight, and response of the individual patient, and the severity of the patient's symptoms. Dosages per day normally fall within the range of about 0.1 to about 10 mg/kg of body weight. In some instances dosage levels below the lower limit of the aforesaid range may be more than adequate, while in other cases still larger doses may be employed. Therefore, the above dosage range is not intended to limit the scope of the invention in any way. This invention also provides a compound of Formula I, or a pharmaceutically acceptable salt thereof, for use as a medicament.

Additionally, this invention provides use of a compound of Formula I, or a pharmaceutically acceptable salt thereof, in the manufacture of a medicament for treating cancer. In particular, these cancers are selected from the group consisting of medulloblastoma, basal cell carcinoma, esophagus cancer, gastric cancer, pancreatic cancer, tract cancer, prostate cancer, breast cancer, small cell lung cancer, non-small cell lung cancer, B-cell lymphoma, multiple myeloma, ovarian cancer, colorectal cancer, liver cancer, kidney cancer and melanoma, Furthermore, this invention provides a pharmaceutical composition comprising a compound of Formula I, or a pharmaceutically acceptable salt thereof, as an active ingredient for treating medulloblastoma, basal cell carcinoma, esophagus cancer, gastric cancer, pancreatic cancer, biliary tract cancer, prostate cancer, breast cancer, small cell lung cancer, non-small cell lung cancer, B-cell lymphoma, multiple myeloma, ovarian cancer, colorectal cancer, liver cancer, kidney cancer or melanoma.

As used herein, the following terms have the meanings indicated: "Et$_2$O" refers to diethyl ether: "DMF" refers to dimethylformamide; "DMSO" refers to dimethylsulfoxide; "TFA" refers to trifluoroacetic acid; "boc" or "t-boc" refers to tert-butoxycarbonyl; "SCX" refers to strong cation exchange; "PyBOP" refers to benzotriazol-1-yloxytripyrrolidino-phosphonium hexafluorophosphate: "prep" refers to preparation; "ex" refers to example; and "IC50" refers to the concentration of an agent that produces 50% of the maximal inhibitory response possible for that agent.

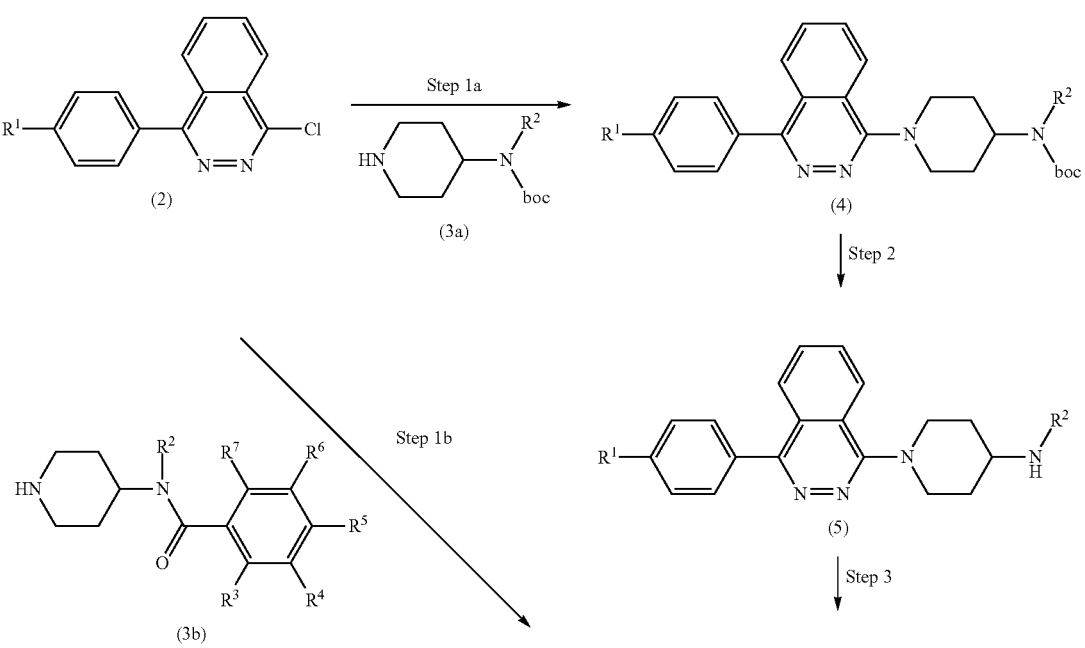

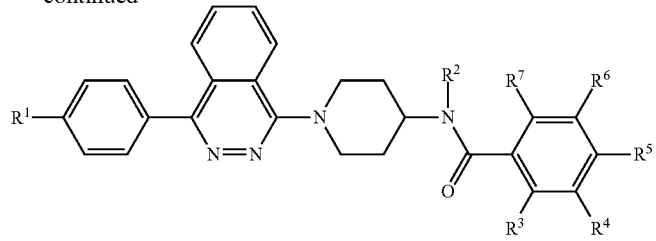

Formula I

A compound of Formula I can be prepared in accordance with reactions as depicted in Scheme 1.

A 1-chloro substituted phthalazine (2) is reacted with a 4-amino boc protected piperidine (3a) in a nucleophilic aromatic substitution (SNAr) to provide a piperidine substituted phthalazine of formula (4). For example, the chloride (2) can be reacted with the piperidine of formula (3a) in a dipolar aprotic solvent such as DMF or DMSO, in the presence of an organic base such as triethylamine or inorganic base such as potassium carbonate and heated to 100-140° C.

Amine functionality, such as that present in the piperidinyl phthalazine of formula (4), can be deprotected and further reacted to give additional compounds of the invention. Methods for introducing and removing nitrogen and oxygen protecting groups are well known in the art (see, e.g., Greene and Wuts, *Protective Groups in Organic Synthesis*, 3$^{rd}$ Ed., John Wiley and Sons, New York, (1999)). For example, boc deprotection of the amino piperidinyl phthalazine of formula (4) can be accomplished under acidic conditions, such as hydrogen chloride or trifluoroacetic acid. Alternatively, HCl can be generated in situ by dropwise addition of acetyl chloride to a solution of an alcohol solvent such as methanol in toluene at 0-20° C. followed by the addition of a compound of formula (4) and heating the solution to 30-60° C. to give a compound of formula (5). It will be obvious to one skilled in the art that a compound of formula (5) can be isolated as a salt such as the hydrochloride amine salt and carried on to Step 3 or transformed to the live amine using an inorganic base such as potassium carbonate. The 4-amino piperidine can be acylated using a substituted beuzoyl chloride in an inert solvent such as dichloromethane or dioxane and a base such as triethylamine or pyridine to give an amide compound of Formula I. Alternatively, a compound of formula (5) can be acylated using a substituted benzoic acid with an appropriate coupling reagent such as PyBOP and an appropriate base such as triethylamine in an inert solvent such as dichloromethane or using 1-(3-dimethylaminopropyl)-3-ethylcarbodiimide hydrochloride and 1-hydroxybenzotriazole in a dipolar aprotic solvent such as DMF.

Alternatively, a 1-chloro substituted phthalazine (2) is reacted with an N-piperidine-4-yl-benzamide of formula (3b) in a nucleophilic aromatic substitution (SNAr) as previously described for Step 1a to directly a compound of Formula I. For example, the chloride (2) can be reacted in a dipolar aprotic solvent such as DMF or DMSO, with a N-piperidine-4-yl-benzamide of formula (3b), in the presence of a base such as triethylamine and heated to 80-140° C. to give an amide of Formula I.

It will be appreciated by the skilled artisan that compounds of formula (2) in Scheme I are commercially available or can be readily prepared by methods similar to those described herein or by using procedures that are established in the art. For example, a 2-phenylcarbonyl benzoic acid, generated from a Grignard reaction of a phenyl bromide with plathalic anhydride, can be cyclized with hydrazine to give a 4-phenyl-2H-phthalazin-1-one. Subsequent treatment with phosphorous oxychloride provides the 1-chloro-4-phenyl-phthalazine of formula (2). Alternatively, 1,4-dichlorophthalazine can be reacted with a phenyl boronic acid in a Suzuki cross-coupling reaction to give the corresponding 1-chloro-4-phenyl-phthalazine of formula (2).

Scheme 2

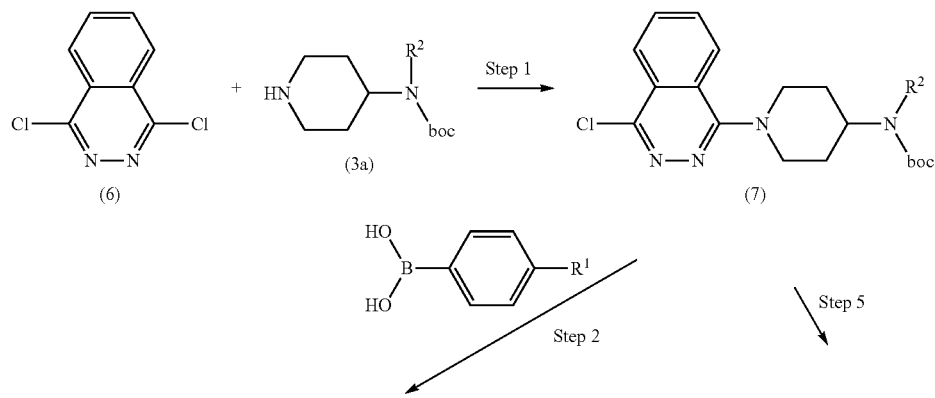

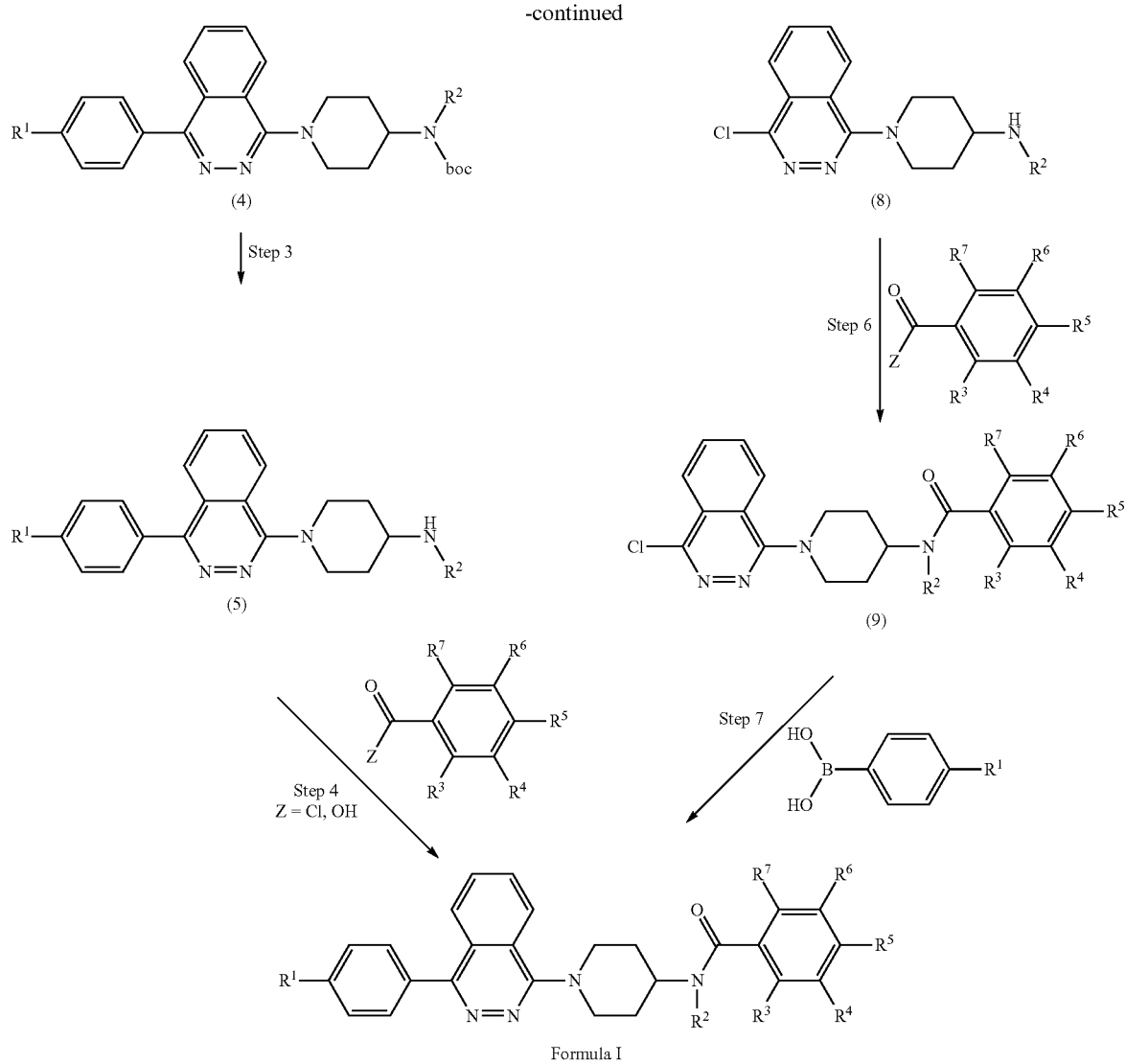

A compound of Formula can be prepared in accordance with reactions as depicted in Scheme 2. In Step 1, a 1,4-dichlorophthalazine (6) can be reacted with a 4-amino boc protected piperidine (3a) in a dipolar aprotic solvent such as N-methylpyrrolidone or DMSO with an appropriate base such as potassium carbonate or triethylamine. The mixture is heated at 70-95° C. to give a compound of formula (7). In one method, shown in Step 5, a compound of formula (7) can be deprotected and subsequently acylated at the amine in Step 6 using a substituted benzoyl chloride in an inert solvent such as dichloromethane, with a base such as triethylamine to give an amide of formula (9). Alternatively, a compound of formula (7) can be acylated using a substituted phenyl carboxylic acid and an appropriate coupling reagent such as PyBOP and a suitable base such as triethylamine in an inert solvent such as dichloromethane room temperature or using 1-hydroxybenzotriazole and 1-(3-dimethylaminopropyl)-ethylcarbodiimide hydrochloride with an appropriate solvent such as DMF. In Step 7, the phthalazinyl chloride of formula (9) is reacted with a phenylboronic acid under Suzuki-Miyaura cross coupling conditions. The skilled artisan will recognize that there are a variety of conditions useful for facilitating such cross-coupling reactions. The reaction conditions make use of a suitable solvent such as dioxane/water. The reaction is accomplished in the presence of a base such as potassium phosphate tribasic monohydrate, sodium carbonate, potassium carbonate, or cesium carbonate. The reaction takes place in the presence of a palladium catalyst such as tris(dibenzylideneacetone)dipalladium (0) with tricyclohexylphosphine or (SP-4-1)-bis[bis(1,1-dimethylethyl) (4-methoxyphenyl)phosphine-κP]dichloro-palladium (prepared according to the synthesis of catalyst D in *J. Org. Chem.* 2007, 72, 5104-5112) under an inert atmosphere at a temperature of about 80-160° C. to give a compound of Formula I.

Alternatively, the plythalazinyl chloride of formula (7) can be initially coupled with a phenyl boronic acid as shown in Step 2 under Suzuki-Miyaura conditions as described previously to give a phenylphthalazine of formula (4). In Step 3, a compound of formula (4) can be deprotected and then acylated as shown in Step 4 at the amine using a substituted benzoyl chloride or phenyl carboxylic acid as described previously to give a compound of Formula I.

The following Preparations and Examples are provided to illustrate the invention in further detail and represent typical

Preparation 1

{1-[4-(4-Fluoro-phenyl)phthalazin-1-yl]piperidin-4-yl}-methyl-carbamic acid tert-butyl ester

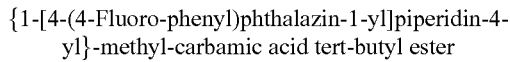

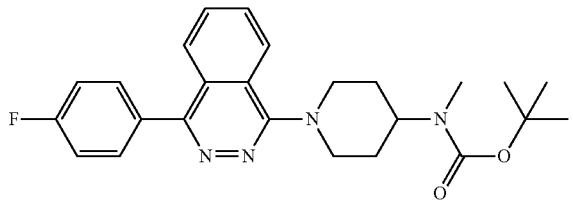

Add 1-chloro-4-(4-fluorophenyl)-phthalazine (3.00 g, 11.6 mmol) to a solution of methyl-piperidin-4-yl-carbamic acid tert-butyl ester (2.98 g, 13.9 mmol) and triethylamine (3.52 g., 34.8 mmol) in DMF (30 mL). Heat at 130° C. for 3 days. Dissolve the reaction mixture in dichloromethane and wash with brine. Dry the organic phase with sodium sulfate, filter, and concentrate under reduced pressure. Purify the resulting residue by flash chromatography (20:5:1, hexane:ethyl acetate: 2 M ammonia in methanol) to yield the title compound as a solid (4.45 g, 88%). ES/MS m/z 437.2 (M+1).

Alternate procedure:

Combine methyl-piperidin-4-yl-carbamic acid tert-butyl ester (75 g, 349 mmol), 1-chloro-4-(4-fluoro-phenyl)-phthalazine (75 g, 289 mmol), and potassium carbonate (80 g, 579 mmol) in dimethyl sulfoxide (500 mL) and heat the mixture to 110° C. for 3 h. Cool the reaction to ambient temperature and pour the slurry into water (1.0 L). Collect the solids by filtration and dry in a vacuum oven for 3 days to provide the title compound as a white solid (120 g, 95%). ES/MS m/z 437.3 (M+1).

Prepare the piperidinylphthalazines in the table below by essentially following the procedure described in Preparation 1, using the appropriate chlorophthalazine and tBOC protected aminopiperidine:

| Prep | Chemical name | ES/MS m/z |
|---|---|---|
| 2 | Methyl-[1-(4-phenylphthalazin-1-yl)-piperidin-4-yl]-carbamic acid tert-butyl ester | 419.2 (M + 1) |
| 3 | tert-Butyl 1-(4-(4-fluorophenyl)phthalazin-1-yl)piperidin-4-ylcarbamate | 423.2 (M + 1) |
| 4 | tert-Butyl 1-(4-phenylphthalazin-1-yl)piperidin-4-ylcarbamate | 405.2 (M + 1) |

Preparation 5

{1-[4-(4-phenyl)phthalazin-1-yl]piperidin-4-yl}methylamine

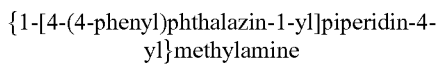

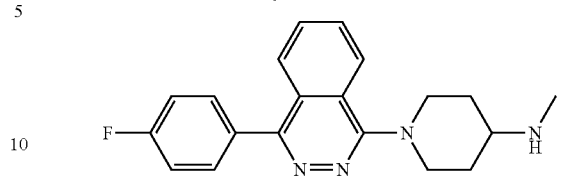

Add trifluoroacetic acid (100 mL) to a solution of {1-[4-(4-fluoro -phenyl) phthalazin-1-yl]-1-piperidin-4-yl}-methyl-carbamic acid tert-butyl ester (11.2 g, 10.2 mmol) in dichloromethane (100 mL). Stir the reaction at room temperature overnight, and concentrate under reduced pressure. Dissolve the resulting residue in dichloromethane and wash with 1 N NaOH and brine. Dry the organic phase with sodium sulfate, filter, and concentrate under reduced pressure. Crystallize the title compound from hexane/dichloromethane to obtain the title compound (8.46 g, 98%). ES/MS m/z 337.2 (M+1).

Alternate Procedure (isolated as the hydrochloride):

Combine toluene (500 mL) and methanol (30 mL) at 10° C. Add acetyl chloride (29 mL, 410 mmol) dropwise over 20 min. Maintain the temperature below 15° C. during the addition. Add {1-[4-(4-fluoro-phenyl)-phthalazin-1-yl]-piperidin-4-yl}-methyl -carbamic acid tert-butyl ester (71 g, 164 mmol). Heat the slurry to 35° C. for 2 h. Cool the slurry to ambient temperature and collect the solid by filtration. Dry in a vacuum oven at 40° C. for 12 h to provide the title compound as a white solid (58 g, 95%), ES/MS m/z 337 (M+1).

Prepare the unprotected aminopiperidinylphthalazines in the table below by essentially following the procedure described in Preparation 5, using the appropriate tBOC protected aminopiperidinylphthalazine:

| Prep | Chemical name | ES/MS m/z |
|---|---|---|
| 6 | Methyl-[1-(4-phenylphthalazin-1-yl)piperidin-4-yl]-amine | 319.2 (M + 1) |
| 7 | 1-(4-(4-Fluorophenyl)phthalazin-1-yl)piperidin-4-amine | 323.2 (M + 1) |
| 8 | 1-(4-Phenylphthalazin-1-yl)piperidin-4-amine | 305.2 (M + 1) |

Preparation 9 tert-Butyl 1-(4-chlorophthalazin-1-yl)piperidin-4-yl (methyl)carbamate

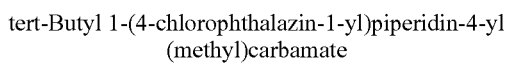

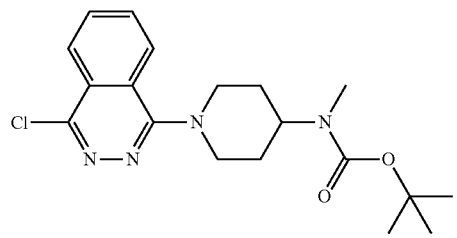

Combine 1,4-dichlorophthalazine (5.00 g, 24.6 mmol), tert-butyl methyl(piperidin-4-yl)carbamate (5.54 g, 25.8 mmol), and potassium carbonate (29,5 mmol; 4.08 g) N-methylpyrrolidone (50.0 mL). Heat the reaction mixture at 80°

C. for 3 days and pour the reaction mixture into ice water. Filter via vacuum filtration to obtain a yellowish solid and dry at room temperature in a vacuum oven. Purify by silica gel chromatography (1:1, hexane:ethyl acetate) to obtain the desired product (5.79 g, 62%), ES/MS m/z 377.2 (M+1).
Alternate Procedure:

Combine 1, 4-dichlorophthalazine (7.04 g, 35.4 mmol), tert-butyl methyl(piperidin-4-yl)carbamate (5.54 g, 37.2 mmol), triethylamine (7.4 mL, 53.1 mmol) and DMSO (85 mL). Heat the reaction mixture at 85° C. for 3 days or until complete consumption of starting material. After cooling, transfer the reaction mixture to a separatory funnel with diethyl ether and wash with water. Separate the organic layer and dry with MgSO$_4$, filter, then concentrate in vocuo. Purify the resulting residue by flash chromatography (0-10% methanol in dichloromethane) to obtain the tide compound (7.6 g, 57%). ES/MS m/z 377.2 (M+1.).

Preparation 10 tert-Butyl methyl(1-(4-(4-(trifluoromethyl)phenyl) phthalazin-1-yl)piperidin-4-yl)carbamate

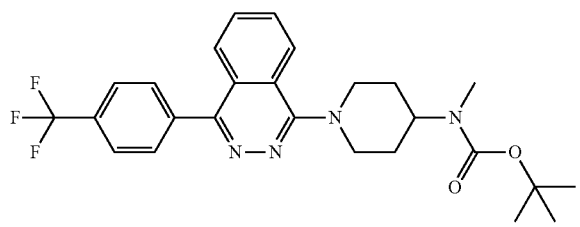

Charge a microwave vessel with tert-butyl 1-(4-chlorophthalazin-1-yl)piperidin-4-yl (methyl)carbamate (0.201 g, 0.534 mmol 4-(trifluoromethyl)phenylboronic acid (122 mg. 0.640 mmol), potassium phosphate tribasic monohydrate (209 mg, 0.907 mmol), tricyclohexylphosphine (19 mg 0.064 mmol), 1,4-dioxane (3.5 mL) and water (1.5 mL). Bubble nitrogen through the reaction mixture for 5 min. Add tris (dibenzylideneacetone)dipalladium (0) (0.027 mmol. 25 mg). Bubble nitrogen through the reaction mixture for another 5 min. Heat the sealed reaction vessel in a microwave for one hour at 150° C. Pass the reaction mixture through a silica gel pad eluting with ethyl acetate. Concentrate in vacuo and purify the resulting residue using silica gel chromatography (30:70, ethyl auctate:hexane) to obtain the title compound (0.170 g (65%). ES/MS m/z 486.8 (M+1).

Preparation 11

N-Methyl-1-(4-(4-(triflouromethyl)phenyl)phthalazin-1-yl)piperidin-4-amine dihydrochloride Add hydrogen chloride (4.0 N in dioxane, 20 mL:, 80.0 mmol) to tert-butyl methyl (1-(4-(4-triflouromethyl)phenyl) phthalazin-1-yl)piperidin-4- yl)carbamate (0.158 g, 0.325 mmol). Stir at room temperature overnight. Remove solvents under reduced pressure. Use the crude material (0.169 g, >100%) as is ES/MS m/z 387.0 (M+1).

Preparation 12 tert-Butyl 1-(4-(4-cyanophenyl)phthalazin-1-yl)piperdin-4-yl(methyl)carbamate

Charge a pressure tube with tert-butyl 1-(4-chlorophthalazin-1-yl)piperidin -4-yl (methyl)carbamate (400 mg, 1.06 mmol), 1,4-dioxane (12 mL), water (4 mL), 4-cyanophenylboronic acid (467 mg, 3.18 mmol), and cesium carbonate (1.40 g, 4.24 mmol). Bubble nitrogen through the reaction mixture for 5 min. Add (SP-4-1)-bis[bis (1,1-dimethylethyl)(4-methoxyphenyl)phosphine-κP]dichloro-palladium (J. Org. Chem. 2007, 72, 5104-5112) (36.0 mg., 0.053 mmol). Bubble nitrogen through the reaction mixture for a few minutes and seal the reaction vessel. Heat the reaction at 90° C. overnight. Filter the reaction mixture through a silica gel pad eluting with ethyl acetate. Remove the solvents under reduced pressure and purify the resulting, residue using silica gel chromatography (30:70, ethyl acetate:hexane) to obtain the title compound (0.392 g, 83%). ES/MS m/z 444.2 (M+1).

Preparation 13

4-(4-(4-(Methylamino)piperidin-1-yl)phthalazin-1-yl)benzonitrile dihydrochloride Prepare the title compound, by essentially following the procedure as described in Preparation 11 using tert-butyl 1-(4-(4-cyanophenyl)phthalazin-1-yl)piperidin-4-yl (methyl)carbamate (0.385 g, 0.868 mmol). Use the crude material (0.378 g, >100%) as is in subsequent reactions. ES/MS m/z 344.2 (M+1).

Preparation 14

1-(4-Chloroplithalazin-1-yl)-N-methylpiperidin-4-amine dihydrochloride

Add hydrogen chloride (4.0 N in dioxane, 100 mL; 400 mmol) to a solution of tert-butyl 1-(4-chlorophthalazin-1-yl) piperidin-4-yl(methyl)carbamate (7.60 g; 100 equiv; 20.2 mmol) in methanol (100 mL). Stir at room temperature one hour. Remove the solvent under reduced pressure to obtain the title compound (7.05 g, 100%). ES/MS m/z 277.2 (M+1).

Preparation 15

N-(1-(4-Chlorophthalazin-1-yl)piperidin-4-yl)-N-methyl-2-(trifluoromethyl)benzamide

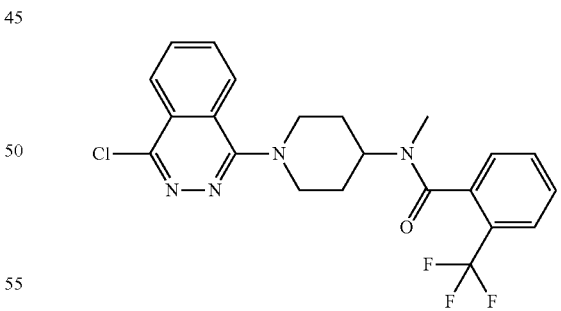

Combine 1-(4-chlorophthalazin-1-yl)-N-methylpiperidin-4-amine dihydrochloride (1.01 g, 2.89 mmol) and triethylamine (1,2 mL, 8.61 mmol) in dichloromethane (30 mL). Flush the reaction vial with nitrogen and add 3-trifluoromethylbenzoyl chloride (0.46 mL, 3.12 mmol). Place the reaction under a nitrogen blanket and stir at room temperature overnight. Concentrate to a residue and purify using silica gel chromatography (0-10% methanol in dichloromethane) to obtain the title compound (1.11 g, 86%). ES/MS m/z 449.2 (M+1).

Prepare the amides in the table below by essentially following the procedure described in Preparation 15, using the appropriate acid chloride:

| Prep | Chemical name | ES/MS m/z |
|------|---------------|-----------|
| 16 | N-(1-(4-Chlorophthalazin-1-yl)piperidin-4-yl)-3-cyano-N-methylbenzamide | 406.2 (M + 1) |
| 17 | N-(1-(4-Chlorophthalazin-1-yl)piperidin-4-yl)-5-fluoro-N-methyl-2-(trifluoromethyl)benzamide | 467.2 (M + 1) |
| 18 | N-(1-(4-Chlorophthalazin-1-yl)piperidin-4-yl)-N-methyl-4-(trifluoromethoxy)benzamide | 465.2 (M + 1) |

Example 1

N-(1-(4-(4-Fluorophenyl)phthalazin-1-yl)piperidin-4-yl)-N-methyl-4-(trifluoromethoxy) benzamide hydrochloride

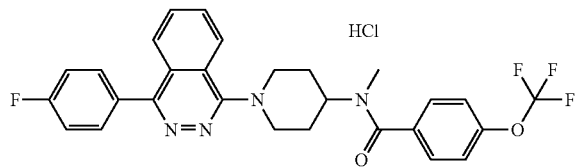

Combine methyl {1-[4-4-fluoro-phenyl)phthalazin-1-yl]piperidin -4-yl}methylamine (100 mg, 0.300 mmol), triethylamine (0.12 mL, 0.89 mmol) and dichloromethane (2 mL) at room temperature. Add 4-(trifluoromethoxy)-benzoyl chloride (100 mg. 0.45 mmol) to the mixture and stir at room temperature overnight. Concentrate the reaction mixture and purify the resulting residue by flash chromatography (20:5:1, hexane:ethyl acetate:2 M ammonia in methanol). Add 1 N HCl in diethyl ether to a solution of the isolated product in dichloromethane/methanol and remove the solvents under a stream of nitrogen gas to yield the title compound as a solid (98 mg. 58%). ES/MS m/z 525.0 (M+1).

Alternate Procedure:

Add {-1[4-(4-fluoro-phenyl)-phthalazin-1-yl]-piperidin-4-yl}-methyl-amine hydrochloride (58 g, 155 mmol) to 1,4-dioxane (580 mL). Add triethylamine (86 mL, 622 mmol) and stir for 20 min. Add 4-(trifluoromethoxy)benzoyl chloride (24 mL, 155 mmol) dropwise over a period of 20 min. Stir for one hour at ambient temperature. Add water (100 mL), extract with ethyl acetate (200 mL), and concentrate the organic portion under reduced pressure. Purify the resulting residue by flash chromatography, eluting with ethyl acetate over a 1 kg silica plug to yield the product as a colorless oil (58 g, 71%). Combine toluene (586 mL) with ethanol (117 mL) and cool to 3° C. Add acetyl chloride (8 mL 111 mmol) over a period of 20 min. Stir for 20 min and then add N-{1-[4-(4-fluoro-phenyl)-phthalazin-1-yl]-piperidin-4-yl}, -N-methyl -4-trifluoromethoxy -benzamide (58 g, 111 mmol) in toluene (40 mL) in one portion. Stir for 12 h. Concentrate to ⅓ volume. Collect the precipitate by filtration. Dry the solid in a vacuum oven at 40° C. overnight to afford the title compound as a whim solid (42 g. 67%), ES/MS m/z 525.0 (M+1).

Prepare the amides m the table below, by essentially following the procedure described in Example 1, using the appropriate acid chloride:

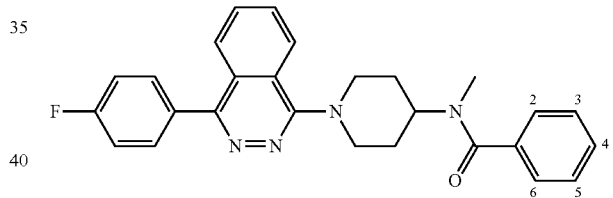

| Ex | Chemical name | Benzamide substituents | ES/MS m/z |
|----|---------------|------------------------|-----------|
| 2 | N-(1-(4-(4-Fluorophenyl)phthalazin-1-yl)piperidin-4-yl)-N-methyl-4-(trifluoromethyl)benzamide hydrochloride | 4-$CF_3$ | 509.2 (M + 1) |
| 3 | N-(1-(4-(4-Fluorophenyl)phthalazin-1-yl)piperidin-4-yl)-N-methyl-3-(trifluoromethyl)benzamide hydrochloride | 3-$CF_3$ | 509.2 (M + 1) |
| 4 | N-(1-(4-(4-Fluorophenyl)phthalazin-1-yl)piperidin-4-yl)-N-methyl-2-(trifluoromthyl)benzamide hydrochloride | 2-$CF_3$ | 509.2 (M + 1) |
| 5 | N-(1-(4-(4-Fluorophenyl)phthalazin-1-yl)piperidin-4-yl)-N-methyl-2-(trifluoromethoxy)benzamide hydrochloride | 2-$OCF_3$ | 525.2 (M + 1) |
| 6 | 2,6-Difluoro-N-(1-(4-(4-fluorophenyl)phthalazin-1-yl)piperidin-4-yl)-N-methylbenzamide hydrochloride | 2-F, 6-F | 477.2 (M + 1) |
| 7 | 2-Fluoro-N-(1-(4-(4-fluorophenyl)phthalazin-1-yl)piperidin-4-yl)-N-methyl-6-(trifluoromethyl)benzamide hydrochloride | 2-F, 6-$CF_3$ | 527.2 (M + 1) |
| 8 | N-(1-(4-(4-Fluorophenyl)phthalazin-1-yl)piperidin-4-yl)-N-methyl-2,5-bis(trifluoromethyl)benzamide hydrochloride | 2-$CF_3$, 5-$CF_3$ | 576.8 (M + 1) |
| 9 | 2-Fluoro-N-(1-(4-(4-fluorophenyl)phthalazin-1-yl)piperidin-4-yl)-N-methyl-4-(trifluoromethyl)benzamide hydrochloride | 2-F, 4-$CF_3$ | 527.0 (M + 1) |

-continued

| Ex | Chemical name | Benzamide substituents | ES/MS m/z |
|----|---------------|------------------------|-----------|
| 10 | 2,4-Dichloro-N-(1-(4-(4-fluorophenyl)phthalazin-1-yl)piperidin-4-yl)-N-methylbenzamide hydrochloride | 2-Cl, 4-Cl | 509.0 (M + 1) |
| 11 | 2,4,6-Trifluoro-N-(1-(4-(4-fluorophenyl)phthalazin-1-yl)piperidin-4-yl)-N-methylbenzamide hydrochloride | 2-F, 4-F, 6-F | 495.0 (M + 1) |
| 12 | 5-Fluoro-N-(1-(4-(4-fluorophenyl)phthalazin-1-yl)piperidin-4-yl)-N-methyl-2-(trifluoromethyl)benzamide hydrochloride | 2-CF$_3$, 5-F | 527.0 (M + 1) |
| 13 | 3-Fluoro-N-(1-(4-(4-fluorophenyl)phthalazin-1-yl)piperidin-4-yl)-N-methyl-4-(trifluoromethyl)benzamide hydrochloride | 3-F, 4-CF$_3$ | 527.0 (M + 1) |
| 14 | 2-Fluoro-N-(1-(4-(4-fluorophenyl)phthalazin-1-yl)piperidin-4-yl)-N-methyl-3-(trifluoromethyl)benzamide hydrochloride | 2-F, 3-CF$_3$, | 527.0 (M + 1) |
| 15 | 2-Chloro-N-(1-(4-(4-fluorophenyl)phthalazin-1-yl)piperidin-4-yl)-N-methyl-5-(trifluoromethyl)benzamide, hydrochloride | 2-Cl, 5-CF$_3$ | 543.0 (M + 1) |
| 16 | 3-Chloro-2-fluoro-N-(1-(4-(4-fluorophenyl)phthalazin-1-yl)piperidin-4-yl)-N-methyl-6-(trifluoromethyl)benzamide hydrochloride | 2-F, 3-Cl, 6-CF$_3$ | 561.0 (M + 1) |
| 17 | N-(1-(4-(4-Fluorophenyl)phthalazin-1-yl)piperidin-4-yl)-N-methyl-3-(trifluoromethoxy)benzamide hydrochloride | 3-OCF$_3$ | 525.2 (M + 1) |
| 18 | 2-Chloro-N-(1-(4-(4-fluorophenyl)phthalazin-1-yl)piperidin-4-yl)-N-methylbenzamide hydrochloride | 2-Cl | 475.0 (M + 1) |
| 19 | 3-Chloro-N-(1-(4-(4-fluorophenyl)phthalazin-1-yl)piperidin-4-yl)-N-methylbenzamide hydrochloride | 3-Cl | 475.0 (M + 1) |
| 20 | 4-Chloro-N-(1-(4-(4-fluorophenyl)phthalazin-1-yl)piperidin-4-yl)-N-methylbenzamide hydrochloride | 4-Cl | 475.0 (M + 1) |
| 21 | 2,4-Difluoro-N-(1-(4-(4-fluorophenyl)phthalazin-1-yl)piperidin-4-yl)-N-methylbenzamide hydrochloride | 2-F, 4-F | 477.0 (M + 1) |
| 22 | 2-Fluoro-N-(1-(4-(4-fluorophenyl)phthalazin-1-yl)piperidin-4-yl)-N-methyl-5-(trifluoromethyl)benzamide hydrochloride | 2-F, 5-CF$_3$ | 527.0 (M + 1) |
| 23 | N-(1-(4-(4-Fluorophenyl)phthalazin-1-yl)piperidin-4-yl)-N-methyl-2,4-bis(trifluoromethyl)benzamide hydrochloride | 2-CF$_3$, 4-CF$_3$ | 577.0 (M + 1) |
| 24 | 4-Cyano-N-(1-(4-(4-fluorophenyl)phthalazin-1-yl)piperidin-4-yl)-N-methylbenzamide hydrochloride | 4-CN | 466.2 (M + 1) |
| 25 | 2,6-Dichloro-N-(1-(4-(4-fluorophenyl)phthalazin-1-yl)piperidin-4-yl)-N-methylbenzamide hydrochloride | 2-Cl, 6-Cl | 509.0 (M + 1) |
| 26 | 3-Cyano-N-(1-(4-(4-fluorophenyl)phthalazin-1-yl)piperidin-4-yl)-N-methylbenzamide hydrochloride | 3-CN | 466.2 (M + 1) |
| 27 | 4-Chloro-N-(1-(4-(4-fluorophenyl)phthalazin-1-yl)piperidin-4-yl)-N-methyl-2-(trifluoromethyl)benzamide hydrochloride | 2-CF$_3$, 4-Cl | 542.6 (M + 1) |
| 28 | 2,4-Dichloro-5-fluoro-N-(1-(4-(4-fluorophenyl)phthalazin-1-yl)piperidin-4-yl)-N-methylbenzamide hydrochloride | 2-Cl, 4-Cl, 5-F | 526.6 (M + 1) |
| 29 | 5-Chloro-N-(1-(4-(4-fluorophenyl)phthalazin-1-yl)piperidin-4-yl)-N-methyl-2-(trifluoromethyl)benzamide hydrochloride | 2-CF$_3$, 5-Cl | 543.2 (M + 1) |
| 30 | 4-Fluoro-N-(1-(4-(4-fluorophenyl)phthalazin-1-yl)piperidin-4-yl)-N-methyl-2-(trifluoromethyl)benzamide hydrochloride | 2-CF$_3$, 4-F | 527.0 (M + 1) |

Alternate Procedure to Example 30:

Add {1-[4-(4-4-fluoro-phenyl)-phthalazin-1-yl]-piperidin-4-yl}-methyl-amine hydrochloride (80 g, 240 mmol) to water (500 mL) to form a slurry. Add potassium carbonate until the pH is 10, Add methylene chloride (400 mL). Stir vigorously until all the solids dissolve. Separate the organic layer and concentrate to a clear oil (74 g, 220 mmol) to afford 1-[4-(4-fluoro-phenyl)-phthalazin-1-yl]-piperidin-4-yl}-methyl-amine.

Combine {1-[4-(4-fluoro-phenyl)-phthatazin-1-yl]-piperidin-4-yl}-methyl-amine (12 g, 35 mmol), pyridine (20 mL, 247 mmol) and 1,4-dioxane (120 mL). Stir the reaction for 20 min. Add dichloromethane (25 mL). Stir the slurry for 20 min. Add 4-fluoro-2-(trifluoromethyl) benzoyl chloride (6.5 mL, 43 mmol) dropwise over a period of 20 mm. Stir for 2 h. Pour the mixture into water (100 mL), extract with dichloromethane (200 mL) and concentrate under reduced pressure. Purify the residue by flash chromatography (1:1, ethyl acetate:hexane) to yield the product as a white solid (10.3 g, 55%), Add 4-fluoro-N-{1-[4-(4-fluoro-phenyl)-phthalazin-1-yl]-piperidin-4-yl}-N -methyl-2-trifluoromethyl-benzamide (10 g, 19.85 mmol) to toluene (125 mL) to obtain a slurry. Add methanol (30 mL) to make a homogenous solution. Add hydrogen chloride (5.21 mL, 4.0 N in 1,4-dioxane, 20 mmol) in one portion. Allow to stir for one hour and concentrate ⅓ volume. Collect the solid and dry in a vacuum oven for 12 h at 35° C. to obtain the title compound as a white solid (9.5 g, 85%). ES/MS. m/z 527.0 (M+1).

Example 31

4-Fluoro-N-methyl-N-(1-(4-phenylphthalazin-1-yl)piperidin-4-yl)-2-(trifluoromethyl) benzamide hydrochloride Combine methyl-[1-(4-phenylphthalazin-1-yl)piperidin-4-yl]-amine (800 mg, 2.51 mmol), triethylamine (1.05 mL, 7.54 mmol) and dichlaromethane (20 mL) at room temperature. Add 4-fluoro-2-trifluoromethyl)benzoyl chloride (683 mg, 3.01 mmol) to the mixture and stir at room temperature overnight. Concentrate the reaction mixture and purify the resulting residue by flash chromatography (20:5:1, hexane:ethyl acetate:2 M ammonia in methanol), Add 1 N HCl in diethyl ether to a solution of the isolated product in dichloromethanelmethanol. Filter the resulting solid to obtain the tide compound (1.13 g, 88%). ES/MS m/z 509.2 (M+1).

Prepare the amides in the table below by essentially following the procedure described in Example 31 , using the appropriate acid chloride. Isolate the HCl salt by filtration or by evaporating. the solvent:

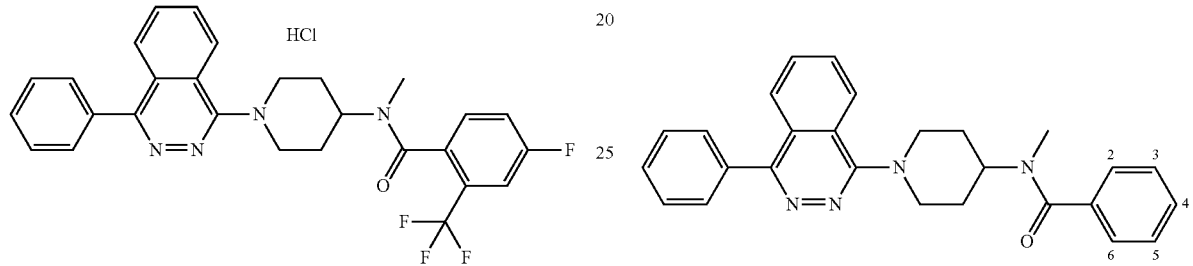

| Ex | Chemical name | Benzamide substituents | ES/MS m/z |
|---|---|---|---|
| 32 | N-Methyl-N-(1-(4-phenylphthalazin-1-yl)piperidin-4-yl)-2-(trifluoromethoxy)benzamide hydrochloride | 2-OCF$_3$ | 507.2 (M + 1) |
| 33 | N-Methyl-N-(1-(4-phenylphthalazin-1-yl)piperidin-4-yl)-4-(trifluoromethoxy)benzamide hydrochloride | 4-OCF$_3$ | 507.2 (M + 1) |
| 34 | N-Methyl-N-(1-(4-phenylphthalazin-1-yl)piperidin-4-yl)-2-(trifluoromethyl)benzamide hydrochloride | 2-CF$_3$ | 491.2 (M + 1) |
| 35 | N-Methyl-N-(1-(4-phenylphthalazin-1-yl)piperidin-4-yl)-3-(trifluoromethyl)benzamide hydrochloride | 3-CF$_3$ | 491.2 (M + 1) |
| 36 | 2-Fluoro-N-methyl-N-(1-(4-phenylphthalazin-1-yl)piperidin-4-yl)-6-(trifluoromethyl)benzamide hydrochloride | 2-F, 6-CF$_3$ | 509.2 (M + 1) |
| 37 | N-Methyl-N-(1-(4-phenylphthalazin-1-yl)piperidin-4-yl)-4-(trifluoromethyl)benzamide hydrochloride | 4-CF$_3$ | 491.2 (M + 1) |
| 38 | 2-Fluoro-N-methyl-N-(1-(4-phenylphthalazin-1-yl)piperidin-4-yl)-4-(trifluoromethyl)benzamide hydrochloride | 2-F, 4-CF$_3$ | 509.2 (M + 1) |
| 39 | 2,4-Dichloro-N-methyl-N-(1-(4-phenylphthalazin-1-yl)piperidin-4-yl)benzamide hydrochloride | 2-Cl, 4-Cl | 491.0 (M + 1) |
| 40 | N-Methyl-N-(1-(4-phenylphthalazin-1-yl)piperidin-4-yl)-2,4-bis(trifluoromethyl)benzamide hydrochloride | 2-CF$_3$, 4-CF$_3$ | 559.2 (M + 1) |
| 41 | 4-Cyano-N-methyl-N-(1-(4-phenylphthalazin-1-yl)piperidin-4-yl)benzamide hydrochloride | 4-CN | 448.2 (M + 1) |
| 42 | 3-Chloro-2-fluoro-N-methyl-N-(1-(4-phenylphthalazin-1-yl)piperidin-4-yl)-6-(trifluoromethyl)benzamide hydrochloride | 2-F, 3-Cl, 6-CF$_3$ | 543.0 (M + 1) |
| 43 | 5-Fluoro-N-methyl-N-(1-(4-phenylphthalazin-1-yl)piperidin-4-yl)-2-(trifluoromethyl)benzamide hydrochloride | 2-CF$_3$, 5-F | 509.2 (M + 1) |
| 44 | N-Methyl-N-(1-(4-phenylphthalazin-1-yl)piperidin-4-yl)-2,5-bis(trifluoromethyl)benzamide hydrochloride | 2-CF$_3$, 5-CF$_3$ | 559.2 (M + 1) |

| Ex | Chemical name | Benzamide substituents | ES/MS m/z |
|---|---|---|---|
| 45 | 2-Chloro-N-methyl-N-(1-(4-phenylphthalazin-1-yl)piperidin-4-yl)-5-(trifluoromethyl)benzamide hydrochloride | 2-Cl, 5-$CF_3$ | 525.2 (M + 1) |
| 46 | 2-Fluoro-N-methyl-N-(1-(4-phenylphthalazin-1-yl)piperidin-4-yl)-5-(trifluoromethyl)benzamide hydrochloride | 2-F, 5-$CF_3$ | 509.2 (M + 1) |
| 47 | 3-Fluoro-N-methyl-N-(1-(4-phenylphthalazin-1-yl)piperidin-4-yl)-4-(trifluoromethyl)benzamide hydrochloride | 3-F, 4-$CF_3$ | 509.2 (M + 1) |
| 48 | 2-Fluoro-N-methyl-N-(1-(4-phenylphthalazin-1-yl)piperidin-4-yl)-3-(trifluoromethyl)benzamide hydrochloride | 2-F, 3-$CF_3$ | 509.2 (M + 1) |

Example 49

N-(1-(4-(4-fluorophenyl)phthalazin-1-yl)piperidin-4-yl)-4-(trifluoromethyl)benzamide hydrochloride

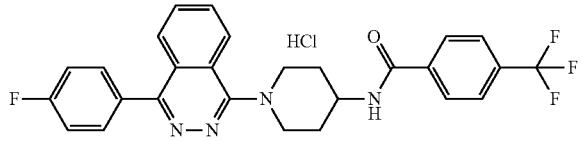

Combine 1-(4-(4-fluorophenyl)phthalazin-1-yl)piperidin-4-amine (110 mg, 0.34 mmol), triethylamine (0.14 mL, 1.02 mmol) and dichloromethane (2 mL) at room temperature. Add 4-(trifluoromethyl)-benzoyl chloride (85 mg, 0.41 mmol) to the mixture and stir at room temperature overnight. Concentrate the reaction mixture and purify the resulting residue by flash chromatography (20:5:1. hexane:ethyl acetate: 2 M ammonia in methanol). Add 1 N HCl in diethyl ether to a solution of the isolated product in dichloromethane/methanol and remove the solvents under a stream of nitrogen gas to yield the title compound as a solid (57 mg, 32%). ES/MS m/z 495.2 (M+1).

Prepare the amides in the table below: by essentially following the procedure as described in Example 49, using the appropriate acid chloride:

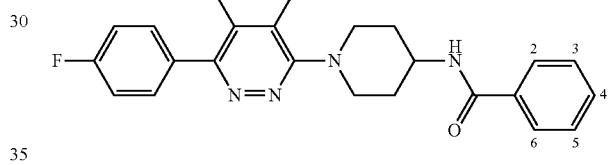

| Ex | Chemical name | Benzamide substituents | ES/MS m/z |
|---|---|---|---|
| 50 | 4-Fluoro-N-(1-(4-(4-fluorophenyl)phthalazin-1-yl)piperidin-4-yl)benzamide hydrochloride | 4-F | 445.2 (M + 1) |
| 51 | N-(1-(4-(4-Fluorophenyl)phthalazin-1-yl)piperidin-4-yl)-3-(trifluoromethyl)benzamide hydrochloride | 3-$CF_3$ | 495.2 (M + 1) |
| 52 | N-(1-(4-(4-Fluorophenyl)phthalazin-1-yl)piperidin-4-yl)-4-(trifluoromethoxy)benzamide hydrochloride | 4-$OCF_3$ | 511.2 (M + 1) |
| 53 | N-(1-(4-(4-Fluorophenyl)phthalazin-1-yl)piperidin-4-yl)-2-(trifluoromethyl)benzamide hydrochloride | 2-$CF_3$ | 495.2 (M + 1) |
| 54 | N-(1-(4-(4-Fluorophenyl)phthalazin-1-yl)piperidin-4-yl)-2-(trifluoromethoxy)benzamide hydrochloride | 2-$OCF_3$ | 511.0 (M + 1) |
| 55 | N-(1-(4-(4-Fluorophenyl)phthalazin-1-yl)piperidin-4-yl)-3-(trifluoromethoxy)benzamide hydrochloride | 3-$OCF_3$ | 511.0 (M + 1) |
| 56 | 4-Cyano-N-(1-(4-(4-fluorophenyl)phthalazin-1-yl)piperidin-4-yl)benzamide hydrochloride | 4-CN | 452.0 (M + 1) |
| 57 | 2,6-Difluoro-N-(1-(4-(4-fluorophenyl)phthalazin-1-yl)piperidin-4-yl)benzamide hydrochloride | 2-F, 6-F | 463.0 (M + 1) |
| 58 | 2-Fluoro-N-(1-(4-(4-fluorophenyl)phthalazin-1-yl)piperidin-4-yl)-6-(trifluoromethyl)benzamide hydrochloride | 2-F, 6-$CF_3$ | 513.0 (M + 1) |
| 59 | 2,4,6-Trifluoro-N-(1-(4-(4-fluorophenyl)phthalazin-1-yl)piperidin-4-yl)benzamide hydrochloride | 2-F, 4-F, 6-F | 481.0 (M + 1) |

-continued

| Ex | Chemical name | Benzamide substituents | ES/MS m/z |
|---|---|---|---|
| 60 | 2-Fluoro-N-(1-(4-(4-fluorophenyl)phthalazin-1-yl)piperidin-4-yl)-5-(trifluoromethyl)benzamide hydrochloride | 2-F, 5-CF$_3$ | 513.0 (M + 1) |
| 61 | 4-Fluoro-N-(1-(4-(4-fluorophenyl)phthalazin-1-yl)piperidin-4-yl)-2-(trifluoromethyl)benzamide hydrochloride | 2-CF$_3$, 4-F | 513.0 (M + 1) |
| 62 | N-(1-(4-(4-Fluorophenyl)phthalazin-1-yl)piperidin-4-yl)-2,4-bis(trifluoromethyl)benzamide hydrochloride | 2-CF$_3$, 4-CF$_3$ | 563.0 (M + 1) |
| 63 | 2-Chloro-N-(1-(4-(4-fluorophenyl)phthalazin-1-yl)piperidin-4-yl)benzamide hydrochloride | 2-Cl | 461.0 (M + 1) |
| 64 | 3-Chloro-N-(1-(4-(4-fluorophenyl)phthalazin-1-yl)piperidin-4-yl)benzamide hydrochloride | 3-Cl | 461.0 (M + 1) |
| 65 | 4-Chloro-N-(1-(4-(4-fluorophenyl)phthalazin-1-yl)piperidin-4-yl)benzamide hydrochloride | 4-Cl | 461.0 (M + 1) |
| 66 | 2,4-Dichloro-5-fluoro-N-(1-(4-(4-fluorophenyl)phthalazin-1-yl)piperidin-4-yl)benzamide hydrochloride | 2-Cl, 4-Cl, 5-F | 512.6 (M + 1) |
| 67 | 4-Chloro-N-(1-(4-(4-fluorophenyl)phthalazin-1-yl)piperidin-4-yl)-2-(trifluoromethyl)benzamide hydrochloride | 2-CF$_3$, 4-Cl | 528.6 (M + 1) |

Example 68

N-(1-(4-Phenylphthalazin-1-yl)piperidin-4-yl)-4-(trifluoromethyl)benzamide hydrochloride

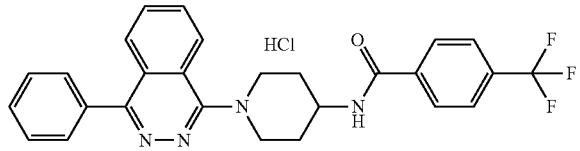

Combine 1-(4-phenylphthalazin-1-yl)piperidin-4-amine (110 mg. 0.34 mmol), triethylamine (0.140 mL, 1.02 mmol), and dichloromethane (2 mL) at room temperature. Add 4-trifluoromethyl)-benzoyl chloride (85 mg, 0.41 mmol) to the mixture and stir at room temperature overnight. Concentrate the reaction mixture and purify the resulting residue by flash chromatography (20:5:1, hexane:ethyl acetate: 2 M ammonia in methanol). Add 1 N HCl in diethyl ether to a solution of the isolated product in dichloromethane/methanol and remove the solvents by placing under a stream of nitrogen gas to yield the title compound as a solid (116 mg, 67%). ES/MS m/z 477.2 (M+1).

Prepare the amides in the table below by essentially following the procedure described in Example 68, using the appropriate acid chloride

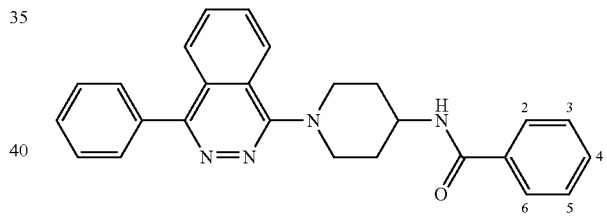

| Ex | Chemical name | Benzamide substituent(s) | ES/MS m/z |
|---|---|---|---|
| 69 | 4-Fluoro-N-(1-(4-phenylphthalazin-1-yl)piperidin-4-yl)benzamide hydrochloride | 4-F | 427.2 (M + 1) |
| 70 | N-(1-(4-Phenylphthalazin-1-yl)piperidin-4-yl)-3-(trifluoromethyl)benzamide hydrochloride | 3-CF$_3$ | 477.2 (M + 1) |
| 71 | N-(1-(4-Phenylphthalazin-1-yl)piperidin-4-yl)-2-(trifluoromethyl)benzamide hydrochloride | 2-CF3 | 477.2 (M + 1) |
| 72 | N-(1-(4-Phenylphthalazin-1-yl)piperidin-4-yl)-2-(trifluoromethoxy)benzamide hydrochloride | 2-OCF$_3$ | 493.0 (M + 1) |
| 73 | N-(1-(4-Phenylphthalazin-1-yl)piperidin-4-yl)-3-(trifluoromethoxy)benzamide hydrochloride | 3-OCF$_3$ | 493.0 (M + 1) |
| 74 | 4-Cyano-N-(1-(4-phenylphthalazin-1-yl)piperidin-4-yl)benzamide hydrochloride | 4-CN | 434.0 (M + 1) |
| 75 | 3-Cyano-N-(1-(4-phenylphthalazin-1-yl)piperidin-4-yl)benzamide hydrochloride | 3-CN | 434.0 (M + 1) |
| 76 | 2,4-Difluoro-N-(1-(4-phenylphthalazin-1-yl)piperidin-4-yl)benzamide hydrochloride | 2-F, 4-F | 445.0 (M + 1) |
| 77 | 2,6-Difluoro-N-(1-(4-phenylphthalazin-1-yl)piperidin-4-yl)benzamide hydrochloride | 2-F, 6-F | 445.0 (M + 1) |
| 78 | 2-Fluoro-N-(1-(4-phenylphthalazin-1-yl)piperidin-4-yl)-6-(trifluoromethyl)benzamide hydrochloride | 2-F, 6-CF$_3$ | 495.0 (M + 1) |

-continued

| Ex | Chemical name | Benzamide substituent(s) | ES/MS m/z |
|---|---|---|---|
| 79 | 2,4,6-Trifluoro-N-(1-(4-phenylphthalazin-1-yl)piperidin-4-yl)benzamide hydrochloride | 2-F, 4-F, 6-F | 463.0 (M + 1) |
| 80 | 2-Fluoro-N-(1-(4-phenylphthalazin-1-yl)piperidin-4-yl)-5-(trifluoromethyl)benzamide hydrochloride | 2-F, 5-CF$_3$ | 495.0 (M + 1) |
| 81 | 4-Fluoro-N-(1-(4-phenylphthalazin-1-yl)piperidin-4-yl)-2-(trifluoromethyl)benzamide hydrochloride | 2-CF$_3$, 4-F | 495.0 (M + 1) |
| 82 | N-(1-(4-Phenylphthalazin-1-yl)piperidin-4-yl)-2,4-bis(trifluoromethyl)benzamide hydrochloride | 2-CF$_3$, 4-CF$_3$ | 545.0 (M + 1) |
| 83 | 2-Chloro-N-(1-(4-phenylphthalazin-1-yl)piperidin-4-yl)benzamide hydrochloride | 2-Cl | 443.0 (M + 1) |
| 84 | 3-Chloro-N-(1-(4-phenylphthalazin-1-yl)piperidin-4-yl)benzamide hydrochloride | 3-Cl | 443.0 (M + 1) |
| 85 | 4-Chloro-N-(1-(4-phenylphthalazin-1-yl)piperidin-4-yl)benzamide hydrochloride | 4-Cl | 443.0 (M + 1) |

Example 86

N-(1-(4-(4-Fluorophenyl)phthalazin-1-yl)piperidin-4-yl)benzamide hydrochloride

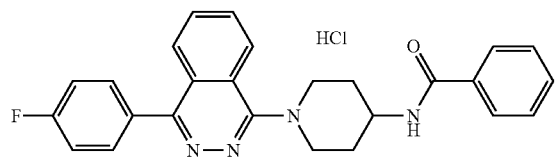

Combine 1-chloro-4-(4-fluorophenyl)phthalazine (150 mg, 0.58 mmol), N-(piperidin-4-yl)benzamide (178 mg, 0.87 mmol), triethylamine (0.404 mL, 2.9 mmol) and dimethylformamide (1 mL) at room temperature. Heat to 100° C. and stir overnight. Pour the crude reaction mixture onto a strong cation exchange Phenomenex Strata® SCX (55 µm, 70 Å) 10 g/60 mL column (with a benzene sulfonic acid functional group). Elute the desired product with 2 N methanolic ammonia (40 mL) and concentrate. Purify the residue by flash chromatography (20-30% [10% 2 N methanolic ammonia in ethyl acetate] in hexane). Add 1 N hydrochloric acid in diethyl ether to a solution of the isolated product in dichloromethane/methanol and remove the solvents under a stream of nitrogen gas to yield the title compound as a solid (137 mg, 51%). ES/MS m/z 427.2 (M+1).

Example 87

N-(1-(4-(4-Cyanophenyl)phthalazin-1-yl)piperidin-4-yl)-4-fluoro-N-methyl-2-(trifluoromethyl)benzamide hydrochloride

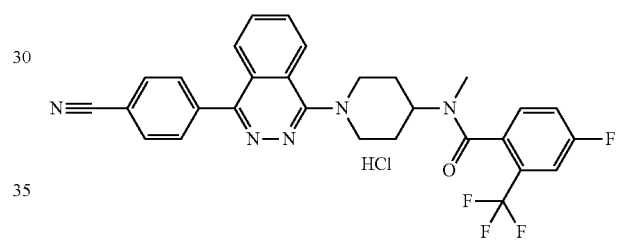

Charge a 4 mL reaction vial with 4-(4-(4-(methylamino)piperidine -1-yl)phthalazin -1-yl)benzonitrile dihydrochloride (44.7 mg, 0.107 mmol), dichloromethane (1 mL), and triethylamine (0.0598 mL, 0.429 mmol). Flush the reaction vial with nitrogen and add 4-fluoro-2-(trifluoromethyl)benzoyl chloride (033 g. 0.14 mmol). Cap the vial and allow the reaction to stir at room temperature overnight. Evaporate to a residue and purify using silica gel chromatography (40:60, ethyl acetate:hexane, then ethyl acetate). Add 1 N HCl in diethyl ether to a solution of the isolated product in dichloromethane/methanol and remove the solvents by placing under a stream of nitrogen gas. Dry in a vacuum oven at 50° C. to obtain the title compound (36.0 mg. 59%). ES/MS m/z 533.8 (M+1).

Prepare the amides in the table below by essentially following the procedure described in Example 87, using the appropriate starting material from Preparation 11 or Preparation 13 and 4-(trifluoromethoxy)benzoyl chloride:

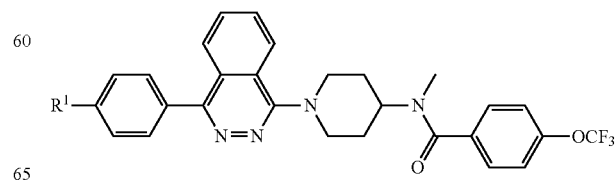

| Ex | Chemical name | Structure | ES/MS m/z |
|---|---|---|---|
| 88 | N-(1-(4-(4-Cyanophenyl)phthalazin-1-yl)piperidin-4-yl)-N-methyl-4-(trifluoromethoxy)benzamide hydrochloride | $R^1$ = CN | 532.2 (M + 1) |
| 89 | N-Methyl-4-(trifluoromethoxy)-N-(1-(4-(4-(trifluoromethyl)phenyl)phthalazin-1-yl)piperidin-4-yl)benzamide hydrochloride | $R^1$ = $CF_3$ | 575.2 (M + 1) |

Example 90

N-Methyl-2-(trifluoromethyl)-N-(1-(4-(4-(triflourmethyl) phenyl)phthalazin-1-yl)piperidin-4-yl)benzamide hydrochloride

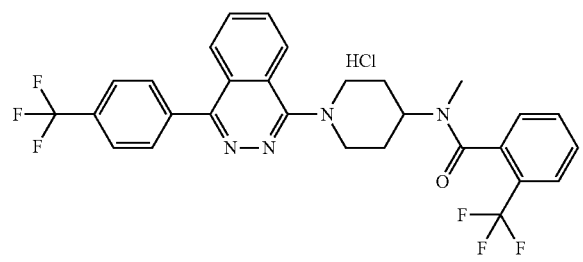

Charge a microwave vessel with N-(1-(4-chlorophthalazin-1-yl)piperidin -4-yl)-N-methyl-2-(trifluoromethyl)benzamide (0.101 g, 0.23 mmol), 4-(trifluoromethyl)phenylboronic acid (0.171 g, 0,9 mmol), cesium carbonate (0.295 g, 0.91 mmol), 1,4-dioxane (3 mL), and water (1 mL). Purge the reaction vial two times with nitrogen. Add (SP-4-1)- bis[bis(1,1-dimethylethyl)(4-methoxyphenyl) phosphine -κP]dichloro-palladium (*J. Org. Chem.* 2007, 72, 5104-5112) (0.002 g; 0.003 mmol) and heat the reaction at 90° C. for 16 h. After cooling, separate the two layers and remove the water. Evaporate the organic solvent with a stream of nitrogen. Purify the residue from the organic layer using silica gel chromatography (0-10% methanol in dichloromethane). Add 4 N HCl in dioxane to a solution of the isolated product in methanol and remove the solvents in vacuo to obtain the title compound (0.100 g, 75%). ES/MS m/z 559.2 (M+1).

Prepare the compounds in the table below, by essentially following the procedures described in Example 90, using the appropriate starting material from Preparations 15-18 and the appropriate boronic acid:

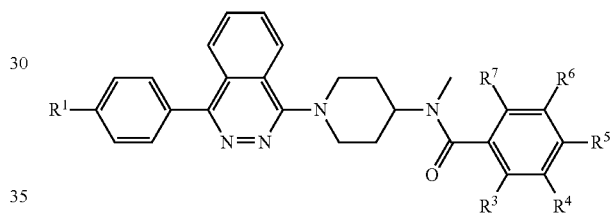

| Ex | Chemical name | R groups ($R^x$ = H unless otherwise indicated) | ES/MS m/z |
|---|---|---|---|
| 91 | 3-Cyano-N-methyl-N-(1-(4-(4-(trifluoromethyl)phenyl)phthalazin-1-yl)piperidin-4-yl)benzamide hydrochloride | $R^1$ = $CF_3$; $R^4$ = CN | 516.2 (M + 1) |
| 92 | N-(1-(4-(4-Cyanophenyl)phthalazin-1-yl)piperidin-4-yl)-N-methyl-2-(trifluoromethyl)benzamide hydrochloride | $R^1$ = CN; $R^3$ = $CF_3$ | 516.2 (M + 1) |
| 93 | N-(1-(4-(4-Cyanophenyl)phthalazin-1-yl)piperidin-4-yl)-5-fluoro-N-methyl-2-(trifluoromethyl)benzamide hydrochloride | $R^1$ = CN; $R^3$ = $CF_3$; $R^6$ = F | 534.2 (M + 1) |
| 94 | 3-Cyano-N-(1-(4-(4-cyanophenyl)phthalazin-1-yl)piperidin-4-yl)-N-methylbenzamide hydrochloride | $R^1$ = CN; $R^4$ = CN | 473.2 (M + 1) |
| 95 | 5-Fluoro-N-methyl-N-(1-(4-(4-(trifluoromethoxy)phenyl)phthalazin-1-yl)piperidin-4-yl)-2-(trifluoromethyl)benzamide hydrochloride | $R^1$ = $OCF_3$; $R^3$ = $CF_3$; $R^6$ = F | 593.2 (M + 1) |
| 96 | N-Methyl-N-(1-(4-(4-(trifluoromethoxy)phenyl)phthalazin-1-yl)piperidin-4-yl)-2-(trifluoromethyl)benzamide hydrochloride | $R^1$ = $OCF_3$; $R^3$ = $CF_3$ | 575.2 (M + 1) |
| 97 | 3-Cyano-N-(1-(4-(4-methoxyphenyl)phthalazin-1-yl)piperidin-4-yl)-N-methylbenzamide hydrochloride | $R^1$ = $OCH_3$; $R^4$ = CN | 478.2 (M + 1) |
| 98 | 3-Cyano-N-methyl-N-(1-(4-(4-(trifluoromethoxy)phenyl)phthalazin-1-yl)piperidin-4-yl)benzamide hydrochloride | $R^1$ = $OCF_3$; $R^4$ = CN | 532.2 (M + 1) |

-continued

| Ex | Chemical name | R groups ($R^x$ = H unless otherwise indicated) | ES/MS m/z |
|---|---|---|---|
| 99 | N-Methyl-4-(trifluoromethoxy)-N-(1-(4-(4-(trifluoromethoxy)phenyl)phthalazin-1-yl)piperidin-4-yl)benzamide hydrochloride | $R^1$ = $OCF_3$; $R^5$ = $OCF_3$ | 591.2 (M + 1) |
| 100 | N-(1-(4-(4-Methoxyphenyl)phthalazin-1-yl)piperidin-4-yl)-N-methyl-4-(trifluoromethoxy)benzamide hydrochloride | $R^1$ = $OCH_3$; $R^5$ = $OCF_3$ | 537.2 (M + 1) |
| 101 | 5-Fluoro-N-(1-(4-(4-methoxyphenyl)phthalazin-1-yl)piperidin-4-yl)-N-methyl-2-(trifluoromethyl)benzamide hydrochloride | $R^1$ = $OCH_3$; $R^3$ = $CF_3$; $R^6$ = F | 539.2 (M + 1) |
| 102 | N-(1-(4-(4-Methoxyphenyl)phthalazin-1-yl)piperidin-4-yl)-N-methyl-2-(trifluoromethyl)benzamide hydrochloride | $R^1$ = $OCH_3$; $R^3$ = $CF_3$ | 521.2 (M + 1) |

The Sonic Hedgehog (Shh) pathway is critical during embryogenesis, but is downregulated after early postnatal development in most tissues. In contrast, more than 30% of human medulloblastoma exhibit high levels of Gli1 (glioma-associated oncogene homolog 1) expression, indicating that abnormal activation of the Shh pathway is important in a subset of pediatric brain tumors. Cerebellar Purkinje cell-secreted Shh promotes the proliferation of granule progenitors, indicating that uncontrolled activation of hedgehog (Hh) pathway may sustain the development of medulloblastoma. This hypothesis is confirmed by the development of medulloblastoma in Patched gene (Pich$^{-/+}$) mice. Treatment of these mice with a hedgehog antagonist inhibited tumor growth. Furthermore, it is documented that hedgehog antagonist treatment resulted in inhibition of Gli1 expression in these brain tumors.

Uncontrolled hedgehog pathway activity has been reported in a number of other cancers as well. For example, hedgehog has been implicated as a survival factor for the following cancers: basal cell carcinoma; upper gastro intestinal tract cancers (esophagus, stomach, pancreas, and biliary tract); prostate cancer; breast cancer: small cell lung cancer; non-small cell lung cancer; B-cell lymphoma; multiple myeloma; gastric cancer; ovarian cancer; colorectal cancer; liver cancer; melanoma; kidney cancer; and medulloblastoma.

Elements of the hedgehog pathway have been asserted to be potential drug targets fir the treatment of cancers. A Daoy cell line established from medulloblastoma tumor (ATCC, HTB-186), is responsive to Hh ligands. When these cells are treated with exogenously added Shh-conditioned media, Rh signaling pathway is activated and results in an increased expression of Gli1. Cyclopamine, an alkaloid isolated from the corn lily Veratrum californicum is a weak hedgehog antagonist and has been shown to suppress the expression of Gli1 in response to Shh stimulation. Recent observations suggest that cyclopamine inhibits the growth of cultured medulloblastoma cells and allografts. Using this Daoy cell model system, potent inhibitors of hedgehog signaling pathways can be identified. Since the compounds of the present invention are hedgehog antagonists, they tire suitable for treating the aforementioned tumor types.

Determination of Biolopical Activity IC50

The following assay protocol and results thereof further demonstrating the utility and efficacy of the compounds and methods of the current invention are given for the purpose of illustration and are not meant to be limiting in any way. Functional assays provide support that the compounds of the present invention exhibit the ability to inhibit Shh signaling.

All ligands, solvents. and reagents employed in the following assay are readily available from commercial. sources or can be readily prepared by one skilled in the art.

Biological activity is determined using a functional assay in Daoy neuronal cancer cells and measures levels of Gli1 ribonucleic, acid via a bDNA. (branched deoxyribonucleic acid) assay system (Panomies, Inc., Fremont, Calif.), Gli was originally discovered in a Glioblastoma cell line and encodes a zinc finger protein that is activated by Shh signaling. The maximum response is obtained by inducing Gli1 transcription in the Daoy cells with conditioned medium (HEK-293 cells stably expressing recombinant Shb) for 24 hours and. then measuring the amount of stimulated Gli1 transcript. The minimum response is the mount of Gli1 transcript inhibited with a control compound in Daoy cells that have been stimulated with conditioned media (human embryonic kidney, (HEK)-293 cells stably expressing recombinant Shh) for 24 hours.

Functional Assay for Measuring the Inhibition of Gli1 in Daoy Cells

The bDNA assay system utilizes the technology of branched-chain DNA to allow amplification of a target ribonucleic acid (transcript). The technology employs three types of synthetic hybrid short Gli1-specific cDNA probes that determine the specificity of the target transcript (capture extenders (CEs), label extenders (LEs), and blockers (BLs)) that hybridize as a complex with the target transcripts to amplify the hybridization signal. The addition of a chemilumigenic substrate during the amplification step allows for detection using luminescence, The Daoy cell line obtained from American Type Culture collection (ATTC) is a Shh-responsive human neuronal tumor cell line and was established in 1985 from a desmoplastic cerebellar medullablastoma tumor, a physiologically relevant tumor cell line. Endogenous levels of Gli1 transcripts levels are low in Daoy cells but can be stimulated by using conditioned media taken from cells stably over-expressing human Shh (a HEK-293 cell line stably transfected with hShh).

Daoy cells are grown to conflunency in tissue culture T225-flasks in Daoy growth media containing Minimum Essential Medium (MEM) plus 10% Fetal Bovine Serum (FBS) with 0.1 nM non-essential amino acids and 1 mM sodium pyruvate. The cells are removed from the T225-flasks using trypsin ethylenediaminetetraacetic acid (EDTA), centrifuged, resuspended in media, and then counted.

The Daoy cells are then seeded at 50,000 cells per well in growth media M Costar 96 well clear tissue culture plates and allowed to incubate overnight at 37 under 5% carbon dioxide ($CO_2$). The cells are washed one time in phosphate buffered saline (PBS) followed by addition of 100 μL of Shh Conditioned Media (Shh-CM) to stimulate levels of Gli1 expression Shh-CM is diluted to achieve maximum stimulation using control growth media—0.1% FBS/DMEM (Dulbeceos Modified Eagle Medium). Daoy cells treated with Shh-CM are then treated with various concentrations of hedgehog inhibitors at concentrations ranging from approximately 1 μM to 0.1 nM. Compounds are allowed to incubate for 24 hours at 37° C. under 5% $CO_2$.

The measurement of the Gli1 transcript is performed by using the Quantigene 2.0 Gli1 assay as described by the manufacturer (Panomics, Inc.). Prepare a diluted lysis mixture (DLM) buffer, which includes Proteinase K. After a 24 hour incubation with compound, the cells are washed one time with PBS and 180 μL of DLM is added to the cells. The cell plate containing the lysis buffer is sealed and placed at 55° C. for 30 to 45 minutes. The resulting cell lysates are then triturated 5 times. A working probe set containing Gli1 probes is made by diluting the probes in the DLM according to manufacturer's directions, and then 20 μL of the working probe set is added to the bDNA assay plates along with 80 μL of the Daoy lysates. The plates are sealed and incubated overnight at 55° C. The bDNA plates are then processed according to the manufacturer's directions. The signal is quantified by reading the plates on a Perkin Elmer Envision reader detecting luminescence. The luminescent signal is directly proportional to the amount of target transcript present in the sample.

The luminescent signal data from the functional assay are used to calculate the IC50 for the in vitro assay. The data are calculated based on the maximum control values (Daoy cells treated with Shh-CM) and the minimum control value (Daoy cells treated with Shh-CM and an inhibitory concentration of a control compound, 1 μM of N-(3-(1H-benzo[d]imidazol-2-yl)4chlorophenyl)-3,5-dimethoxybenzamide). A four parameter logistic curve fit is used to generate the IC50 values using ActivityBase software programs vs. 5.3. equation 205 (Guidance for Assay Development and HTS, vs 5, Copyright 2005. Eli Lilly and Co. and The National Institutes of Health Chemical Genomics Center). The 4 parameter equation is as follows; Fit=(A+((B−A)/(1+((C/x) ^D))) where A=Bottom, B=Top, C=IC50 and D=Hill Coefficient. Following the protocol described, the compounds exemplified herein display an IC50 of <30 nM. The compound of Example 36 has an IC50 of approximately 2.37 nM with a standard error of 0.150 (n=2) in the assay described above. These results provide evidence that the compounds of the present invention are hedgehog antagonists and as such are useful as anticancer agents.

We claim:
1. A compound of the following formula:

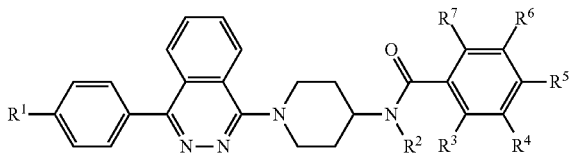

wherein:
R$^1$ is hydrogen, fluoro, cyano, trifluoromethyl, methoxy, or trifluoromethoxy;
R$^2$ is hydrogen or methyl; and
R$^3$, R$^4$, R$^5$, R$^6$ and R$^7$ are independently hydrogen, chloro, fluoro, cyano, trifluoromethyl or trifluoromethoxy, provided that at least two of R$^3$, R$^4$, R$^5$, R$^6$ and R$^7$ are hydrogen;
or a pharmaceutically acceptable salt thereof.

2. The compound of claim 1 wherein R$^1$ is hydrogen, or a pharmaceutically acceptable salt thereof.

3. The compound of claim 1 wherein R$^1$ is fluoro, or a pharmaceutically acceptable salt thereof.

4. The compound of claim 2 wherein R$^2$ is methyl, or a pharmaceutically acceptable salt thereof.

5. The compound of claim 3 wherein R$^2$ is methyl, or a pharmaceutically acceptable salt thereof.

6. The compound of claim 2 wherein R$^2$ is hydrogen, or a pharmaceutically acceptable salt thereof.

7. The compound of claim 3 wherein R$^2$ is hydrogen, or a pharmaceutically acceptable salt thereof.

8. The compound of claim 4 wherein R$^3$ is chloro, fluoro, trifluoromethyl or trifluoromethoxy, or a pharmaceutically acceptable salt thereof.

9. The compound of claim 5 wherein R$^3$ is chloro, fluoro, trifluoromethyl or trifluoromethoxy, or a pharmaceutically acceptable salt thereof.

10. The compound of claim 6 wherein R$^3$ is chloro, fluoro, trifluoromethyl or trifluoromethoxy, or a pharmaceutically acceptable salt thereof.

11. The compound of claim 7 wherein R$^3$ is chloro, fluoro, trifluoromethyl or trifluoromethoxy, or a pharmaceutically acceptable salt thereof.

12. The compound of claim 8 wherein R$^5$ is fluoro, trifluoromethoxy or trifluoromethyl, or a pharmaceutically acceptable salt thereof.

13. The compound of claim 9 wherein R$^5$ is fluoro, trifluoromethoxy or trifluoromethyl, or a pharmaceutically acceptable salt thereof.

14. The compound of claim 10 wherein R$^5$ is fluoro, trifluoromethoxy or trifluoromethyl, or a pharmaceutically acceptable salt thereof.

15. The compound of claim 11 wherein R$^5$ is fluoro, trifluoromethoxy or trifluoromethyl, or a pharmaceutically acceptable salt thereof.

16. The compound of claim 13 which is 4-fluoro-N-(1-(4-(4-fluorophenyl)phthalazin-1-yl)piperidin-4-yl)-N-methyl-2-(trifluoromethyl)benzamide, or a pharmaceutically acceptable salt thereof.

17. A pharmaceutical composition comprising a compound of the formula:

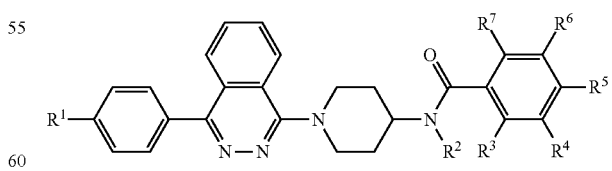

wherein:
R$^1$ is hydrogen, fluoro, cyano, trifluoromethyl, methoxy, or trifluoromethoxy;
R$^2$ is hydrogen or methyl; and
R$^3$, R$^4$, R$^5$, R$^6$ and R$^7$ are independently hydrogen, chloro, fluoro, cyano, trifluoromethyl or trifluoromethoxy, provided that at least two of $R^3$, $R^4$, $R^5$, $R^6$ and $R^7$ are hydrogen; or a pharmaceutically acceptable salt thereof, in combination with a pharmaceutically acceptable carrier, diluent or excipient.

18. The pharmaceutical composition of claim 17 comprising the compound of the formula:

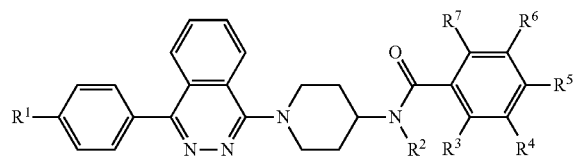

wherein:
R¹ is hydrogen or fluoro;
R² is hydrogen or methyl;
R³ is chloro, fluoro, trifluoromethyl or trifluoromethoxy; and
R⁵ is fluoro, trifluoromethoxy or trifluoromethyl; or a pharmaceutically acceptable salt thereof.

19. The pharmaceutical composition of claim 18 comprising the compound which is 4-fluoro-N-(1-(4-(4-fluorophenyl)phthalazin-1-yl)piperidin-4-yl)-N-methyl-2-(trifluoromethyl)benzamide, or a pharmaceutically acceptable salt thereof.

* * * * *